(12) United States Patent
Fleischmann et al.

(10) Patent No.: US 6,981,989 B1
(45) Date of Patent: Jan. 3, 2006

(54) ROTATABLE AND REVERSIBLY EXPANDABLE SPINAL HYDRAULIC PROSTHETIC DEVICE

(75) Inventors: Lewis W. Fleischmann, Pikesville, MD (US); Christopher Galuardi, Owings Mills, MD (US)

(73) Assignee: X-Pantu-Flex DRD Limited Liability Company, Lutherville, MD (US)

( * ) Notice: Subject to any disclaimer, the term of this patent is extended or adjusted under 35 U.S.C. 154(b) by 132 days.

(21) Appl. No.: 10/419,899

(22) Filed: Apr. 22, 2003

(51) Int. Cl.
*A61F 2/44* (2006.01)

(52) U.S. Cl. ............................. 623/17.11; 623/17.12; 623/17.14

(58) Field of Classification Search ............. 623/17.11, 623/17.12, 17.13, 17.14, 17.15, 17.16
See application file for complete search history.

(56) References Cited

U.S. PATENT DOCUMENTS

| | | | |
|---|---|---|---|
| 3,867,728 A | 2/1975 | Stubstad et al. | |
| 3,875,595 A | 4/1975 | Froning | |
| 4,904,260 A | 2/1990 | Ray et al. | |
| 4,932,975 A * | 6/1990 | Main et al. | 623/17.12 |
| 5,002,576 A | 3/1991 | Fuhrmann et al. | |
| 5,171,278 A | 12/1992 | Pisharodi | |
| 5,171,280 A | 12/1992 | Baumgartner | |
| 5,236,460 A * | 8/1993 | Barber | 623/17.15 |
| 5,344,459 A | 9/1994 | Swartz | |
| 5,458,642 A * | 10/1995 | Beer et al. | 623/17.13 |
| 5,571,189 A | 11/1996 | Kuslich | |
| 5,645,597 A | 7/1997 | Krapiva | |
| 5,683,465 A * | 11/1997 | Shinn et al. | 623/17.14 |
| 5,755,807 A | 5/1998 | Anstaett et al. | |
| 6,063,121 A * | 5/2000 | Xavier et al. | 623/17.15 |
| 6,066,154 A | 5/2000 | Reiley et al. | |
| 6,113,599 A | 9/2000 | Landsberger | |
| 6,375,682 B1 * | 4/2002 | Fleischmann et al. | 623/17.12 |
| 6,395,032 B1 * | 5/2002 | Gauchet | 623/17.12 |
| 6,482,234 B1 | 11/2002 | Weber et al. | |
| 6,527,806 B2 | 3/2003 | Ralph et al. | |
| 6,579,320 B1 * | 6/2003 | Gauchet et al. | 623/17.15 |
| 6,582,466 B1 * | 6/2003 | Gauchet | 623/17.11 |
| 6,733,532 B1 * | 5/2004 | Gauchet et al. | 623/17.12 |
| 2003/0045940 A1 * | 3/2003 | Eberlein et al. | 623/17.16 |
| 2003/0135277 A1 * | 7/2003 | Bryan et al. | 623/17.12 |
| 2004/0093082 A1 * | 5/2004 | Ferree | 623/17.11 |
| 2005/0033437 A1 * | 2/2005 | Bao et al. | 623/17.15 |

FOREIGN PATENT DOCUMENTS

| | | |
|---|---|---|
| DE | 4213771 C1 | 9/1993 |
| EP | 42271 A1 | 12/1981 |
| EP | 305723 A2 | 3/1989 |
| EP | 392076 A1 | 10/1990 |
| EP | 610837 A1 | 8/1994 |

(Continued)

*Primary Examiner*—Eduardo C. Robert
(74) *Attorney, Agent, or Firm*—Rosenberg, Klein & Lee (57) ABSTRACT

An improved spinal intervertebral prosthetic device that offers all degrees of motion afforded by the anatomic spinal intervertebral disc, and by virtue of the incorporation of a dashpot assembly mechanism within reversibly displaceable bellows, provides hydraulic load bearing capability as well as limiting the maximum pressure that can be exerted on the bellows assembly by limiting the compression stroke of the device. The dashpot assembly also increases resistance to lateral shear loading in excess of the bellows convolutions acting alone. The spinal intervertebral prosthetic device absorbs varying axial loads via hydraulic pressure transfer to the bellows convolutions which can flex in a spring-like fashion. Rotational coupling of the upper crown plate and center bearings plate permits normal twisting movements, and spinal flexural freedom is provided by the bellows that are interposed between the center bearings plate and the lower crown plate.

31 Claims, 6 Drawing Sheets

FOREIGN PATENT DOCUMENTS

| | | |
|---|---|---|
| EP | 820740 A1 | 1/1998 |
| EP | 1166725 A2 | 1/2002 |
| FR | 2734148 A1 | 12/1996 |
| WO | WO 9911203 A1 | 3/1999 |
| WO | WO 9922675 A1 | 5/1999 |
| WO | WO 9930651 A1 | 6/1999 |

* cited by examiner

ROTATABLE AND REVERSIBLY EXPANDABLE SPINAL HYDRAULIC PROSTHETIC DEVICE

BACKGROUND OF THE INVENTION

Field of the Invention

The subject invention is directed to the field of prosthetic devices which may be surgically placed internal to the human or other mammalian body.

The subject invention is directed in particular to spinal hydraulic prosthetic devices which may be implanted within a diseased spinal segment of the mammalian body in place of a nucleus pulposus or alternatively may be used to replace a diseased disc in totality.

More particularly, the present invention relates to a rotatable as well as reversibly expandable spinal hydraulic prosthetic device for insertion within the vertebral column of a mammalian body.

Still further, the subject invention directs itself to the field of a spinal disc prosthesis which incorporates some type of biocompatible metallic bellows being filled with a substantially incompressible fluid.

Further, the subject invention relates to a spinal prosthesis having the ability to permit rotation between a pair of vertebrae which are positionally located adjacent to the prosthesis.

Additionally, the subject invention is directed to a prosthetic device which substantially replicates the normal spinal range of motion and tolerates forces in excess of normal ambulatory loads which may be applied to the mammalian body.

The subject invention in particular is directed to a prosthetic device which includes at least one bellows member formed from a multiplicity of rigid washer-like members that minimize shear movement in the lateral direction and in combination resist axial compression by a spring-like action of the bellow convolutions.

Still further, the subject invention directs itself to a prosthetic device which uses and includes bellow members that resist and re-direct axial force loads through the use of a substantially non-compressible fluid for translation of the axial forces to pressure forces for the intent of expanding and flexing the bellows convolutions.

Still further, the subject invention directs itself to a prosthetic device which includes a bellows member and further contains a dashpot assembly mechanism being mounted coaxial with a radial bearing assembly for absorbing and dispersing axial force loads and resisting radial shear forces. Without the dashpot, sudden excessive force loads might cause the bellows to deform, to leak, or even to rupture, with all the attendant risks of major neurologic and/or vascular injury.

Additionally, the subject invention pertains to an implantable spinal prosthetic device having an intervertebral span which is adjustable either pre-insertion during surgical implanting, or subsequent to surgery, where the height is adjustable to individualize and optimize the intervertebral spacing of the affected spinal segment.

PRIOR ART

Implantable spinal prosthetic devices are well known in the art. At present, the primary method employed to remediate degenerative disc disease, discogenic pain, or spinal stenosis is by means of surgical spinal fusion. In this procedure, two or more vertebrae are displaced, the spinal discs between the vertebrae are removed, and crushed bone material taken from the patient's pelvis is inserted between the two vertebrae. This bone material promotes the growth of new bone in the space between the vertebrae. Since this growth takes time, some mechanical means must be incorporated during the surgery to rigidly maintain the proper spacing between the vertebrae as well as carry normal ambulatory loads imposed on the spine by the patient. Insofar as fused vertebrae no longer take part in normal flexing and dispersion of force loads, higher stress loads will now be imposed on the discs and the vertebrae above and below the fused vertebrae thereby accelerating degenerative changes in those nearby spinal levels.

Implantable devices that have been used include semi-rigid elastomeric filler materials sandwiched between two layers of biocompatible metal. The upper and lower plate surfaces generally have multiple spikes for connection to the vertebrae. Other similar devices offer means to screw the upper and lower plates into their conjoining vertebrae and include treated plates to promote bone growth into them. These devices generally permit a small amount of articulation between the vertebrae, but the functional and structural longevity of the elastomeric materials and their bonding agents are often quite short. An ideal prosthesis would last thirty to forty years and withstand about two million cycles per year.

It is the purpose of the subject invention to provide a combination of elements making up an implantable spinal prosthesis having both a long life expectancy and providing for normal articulation within the spine. More particularly, the subject spinal prosthesis allows for tilting from side to side, front to back, minute elongation and compression along a main axial direction and also rotation of the prosthesis about the main axis between the two vertebrae. In addition, the subject spinal prosthesis provides for a means both to dampen sudden excessive axial forces and to resist shearing forces that may accompany activities more vigorous than normal ambulation.

U.S. Pat. No. 6,375,682 is the closest prior art known to applicants, patented by all the inventors of the present patent application and assigned to the same assignee, of which the present patent application is an improvement. The patent is directed at a collapsible, rotatable and expandable spinal hydraulic prosthetic device, which is hydraulically expandable or retractable. The spinal prosthetic device of that invention incorporates a pair of bellows as well as rotationally coupled members that, in combination, affords the patient full and normal range of motion as regards spinal motion-segment articulation. The device as taught is satisfactory for normal ambulatory loads but may under certain circumstances not provide sufficient means for safely accommodating higher than normal force loads. The present subject patent application overcomes the limitation of this prior art by including a dashpot element which allows further stability and tolerance of high force loads in both axial and radial dimensions associated with vigorous activities such as jumping, leaping, running, and so on.

One prior art spinal prosthesis is taught in U.S. Pat. No. 5,002,576, directed to an intervertebral disc prosthesis. This reference is directed to a prosthetic device having a central elastomeric layer sandwiched between two cover plates. The prosthetic device is neither rotatable between the vertebrae, nor does it provide for sufficient bending in the forward, backward or lateral directions.

A recent prior art publication, U.S. Pat. No. 6,527,806, is directed to an intervertebral spacer having a pair of opposing plates in apposition to adjacent vertebrae, and containing at least one spiral-shaped radially diminishing amplitude wave washer as a force restoring element. This device permits only limited rotation and flexural freedom. Furthermore, that non-hydraulic device does not employ a fluid-filled bellows and dashpot mechanism as does the present invention, nor does it utilize ball bearings to facilitate nearly normal twisting movements. In addition, that device does not permit individualized adjustment of the intervertebral spacing as does the present invention.

Another prior art prosthetic implant is shown in U.S. Pat. No. 4,932,975, directed to a vertebral prosthesis. This invention includes an initially flexible bellows which is made inflexible by injection of a fluid that solidifies and, notably, does not permit rotation between the two vertebrae.

U.S. Pat. No. 6,395,032 is directed to an intervertebral disc prosthesis with a liquid chamber. This invention includes bellows containing a liquid and an internal body that absorbs some of the liquid when axial stress is applied to the prosthesis; the prosthesis is attached to the adjacent vertebral bodies by screws lateral to the vertebral bodies. Unlike the present invention, this disc prosthesis lacks a dashpot mechanism and bellows formed from washers, which are designed to obviate lateral displacement of the prosthesis that may result from shearing forces.

U.S. Pat. No. 3,875,595 is directed to an intervertebral disc prosthesis as well as instruments for positioning the same. The prosthesis is a hollow, bladder-like member having the appearance of the natural nucleus of a natural spinal disc (when in an expanded shape). The device does not allow for rotation between vertebrae, thus failing to give the user fully articulated movement.

U.S. Pat. No. 5,571,189 involves an expandable fabric implant for stabilizing the spinal motion segment. The implant is in the form of an inflatable bag positioned within a cavity artificially formed within the spine. The inflatable bag does not permit rotation between the vertebrae.

Another prior art prosthesis is taught in U.S. Pat. No. 5,755,807, being directed to an implantable modular unit and rotating seal for a prosthetic joint. This implant involves a ball-and-socket joint surrounded by a flexible metallic bellows. This system is subject to wear and premature failure due to friction and debris particle buildup associated with the continual rubbing of component parts against each other.

None of the prior art provides for a combination of elements forming a rotatable and reversibly expandable spinal hydraulic prosthetic device that includes a flexible metallic bellows and a dashpot assembly mechanism, which together prevent shear-movement in a lateral direction and tolerate both normal and excessive axial force loads. Additionally, none of the prior art Patents by other inventors provide for a spinal prosthetic device having a ball-bearing mechanism in combination with a bellows and dashpot assembly mechanism, which has the important quality of being flexible and rotatable even under force loads greater than associated with normal ambulation, thereby allowing for substantially normal articulation and range of motion between the two vertebrae.

SUMMARY OF THE INVENTION

The present invention provides for a rotatable and reversibly expandable spinal hydraulic prosthetic device to be implanted between two vertebrae. The spinal prosthetic device includes a flexible metallic bellows positioned between a center bearings plate and a lower crown plate, the center bearings plate being rotationally coupled to an upper crown plate. The upper crown plate and lower crown plate are affixed in a secure fashion to the vertebral bodies above and below the implanted prosthetic device. The center bearings plate is rotationally coupled to the upper crown plate with interposed ball bearings held in position by the bearing retainer, thus allowing for full rotational articulated movement within the spine.

The bellows member(s) is formed from a plurality of rigid washer-like members which help to prevent shear-movement along a lateral direction. The bellows is filled with a biocompatible substantially non-compressible fluid, and may be adjusted to the desired intervertebral distance optimal for an individual patient either prior to, during, or subsequent to the surgical implantation.

It is a principal objective of the subject rotatable and reversibly expandable spinal hydraulic prosthetic device to provide a spinal prosthesis for replacement of a spinal disc.

It is a further objective of the subject spinal prosthetic device to provide a spinal prosthesis having an adjustable axial height.

It is a further objective of the subject invention to provide a spinal prosthesis which permits rotation between the two adjacent vertebrae.

It is a further objective of the subject invention to provide a spinal prosthetic device with means to prevent shear-movement along a lateral direction.

It is an important objective of the present invention to provide a spinal prosthetic device having a threaded fill port or valve member allowing for the variable filling of the prosthesis with incompressible fluids, thus allowing for a variable height of the prosthesis between the two vertebrae and also allowing for variable axial compression-movement within the prosthetic segment.

It is a further important objective of the present invention to provide a spinal prosthetic device having a load bearing capability afforded by a bellows as well as a dashpot assembly mechanism contained therein.

It is an important objective of the present invention to provide a spinal disc prosthetic device having a fluid-containing bellows, formed from convoluted conjoined metallic washer members designed to permit flexural movement and to resist parallel shear movement, although a preformed bellows can also be used.

It is a further important objective of the present invention to provide a spinal prosthetic device having a dashpot with a substantially spherical dashpot element that further resists parallel shear movement and augments the load-bearing tolerances of the invention, the dashpot being centrally located within the fluid-containing dashpot recess formed in the lower crown plate, and the recess being in fluidic continuity with the bellows interior.

It is a further objective of the present invention to provide a bellows of metallic or like composition, that permit flexing of the convolution elements which mimic natural body movements.

It is an objective of the present invention to provide a convolutional bellows design permitting axial height adjustment either pre- or post-implantation with a mechanism to make adjustments to individually fit the patient's intervertebral space requirement.

It is a further objective of the present spinal implant to provide an extension tubing which allows for post implantation intervertebral gap adjustments.

It is an additional objective of the present invention to provide a spinal prosthetic implant device which can be implanted in the space formerly occupied by the nucleus pulposus whereby the annulus fibrosus is left intact.

It is a further objective of the present spinal implant device to provide a system which can be substituted in place of the entire anatomical intervertebral disc, in which case the crown plates are to have a kidney-shaped contour that conforms to the outer edges of the bony vertebral end-plates so as to thereby reduce the heterotopic ossification that may interfere with the range of motion of the affected spinal motion segment.

It is an important objective of the present invention to provide a spinal prosthetic implant with an extended life expectancy, and with no chance of rejection by the body.

DETAILED DESCRIPTION OF THE PREFERRED EMBODIMENTS

Figure 1:
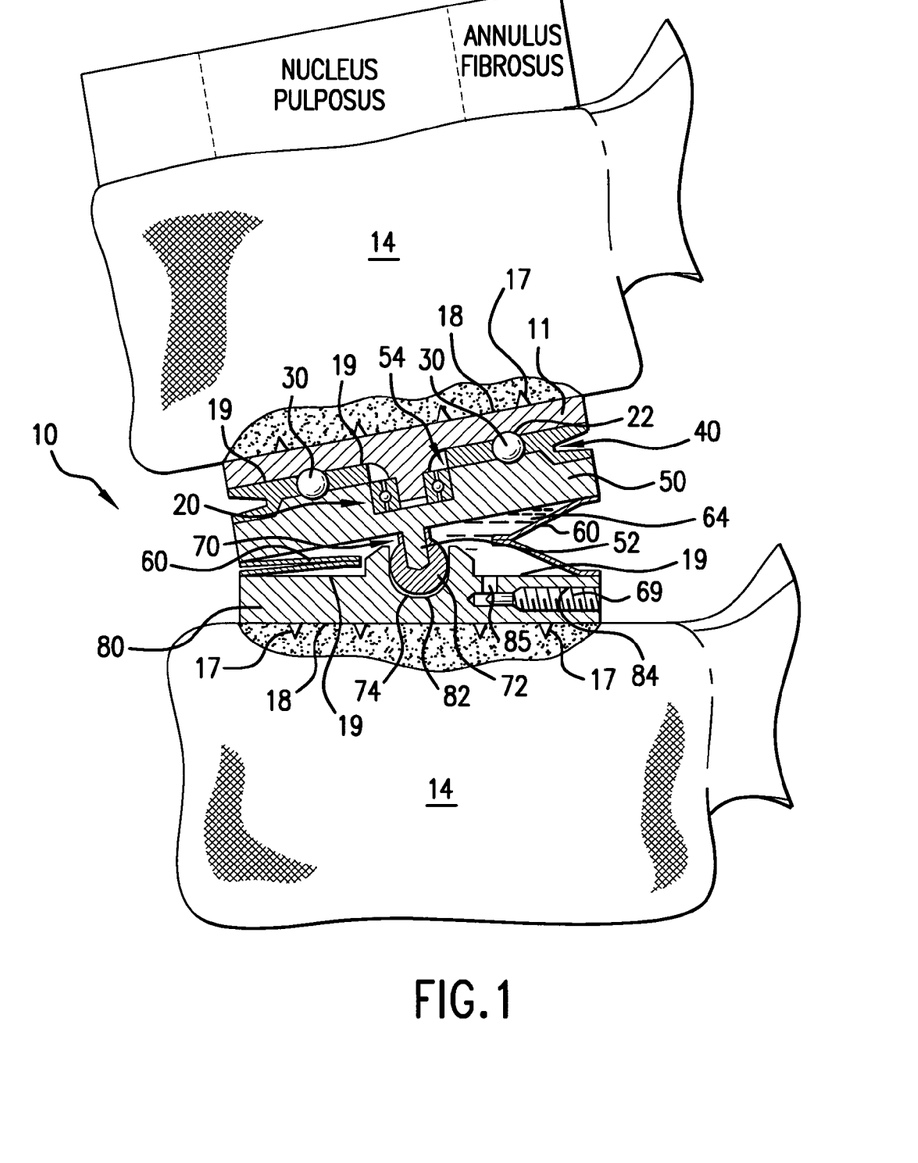
FIG. 1 is a cross-sectional, partially cut-away view of the subject spinal prosthetic device 10 positioned between two vertebrae 14.

FIG. 1 illustrates the preferred embodiment of the spinal prosthetic device 10 implanted between two lumbar vertebrae 14. The preferred embodiment of the device with one bellows 60 is shown in FIG. 1 tilted to its maximum inclination, which may be adjustably varied. The prosthetic device 10 may be used to replace an entire diseased spinal intervertebral disc, or it may be positioned within the nucleus pulposus space of a spinal disc wherein the nucleus pulposus material has been removed. The device 10 is shown in FIG. 1 as it would be located if the annulus fibrosus were left intact. A larger version of this device configuration seen in FIGS. 1 and 4A may be similarly implanted within the space formerly occupied by the entire intervertebral disc, wherein both the nucleus pulposus and the annulus fibrosus are completely removed.

Referring now to FIG. 1, there is shown the rotatable and reversibly expandable spinal hydraulic prosthetic device 10. As shown in FIG. 1, the prosthetic device 10 includes a pair of crown plates, an upper crown plate 11 and a lower crown plate 80, which sandwich between them a center bearings plate 50 which is rotationally coupled by a radial thrust bearing assembly 20 to a bearing retainer seal 40, and at least one bellows member 60. A dashpot mechanism 70 is formed between the center bearings plate 50 and the lower crown plate 80, and is seated in a recess 82 defined in the second surface 19 of the lower crown plate 80.

Figure 2:
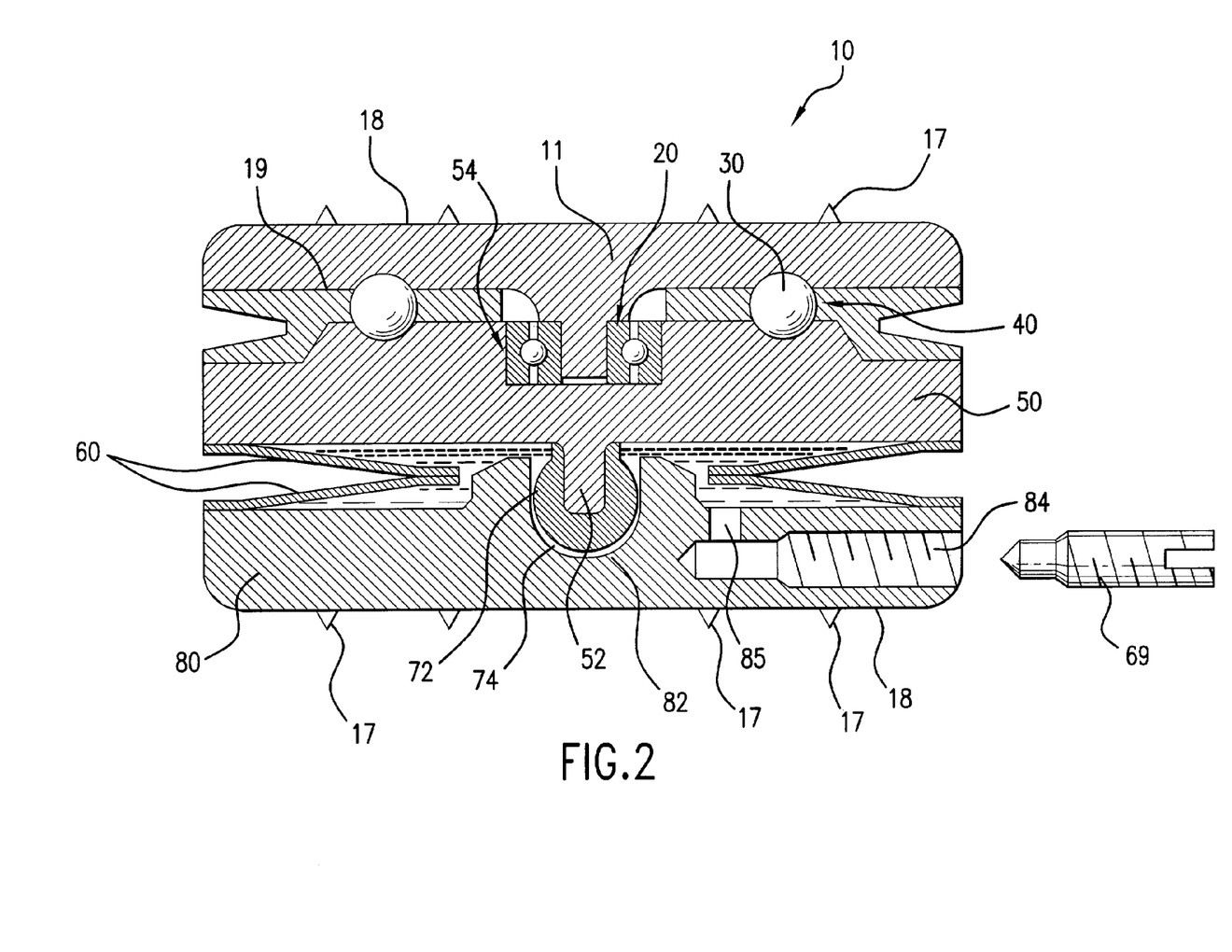
FIG. 2 is a detailed cross-sectional view of the subject spinal prosthetic device 10.
Figure 4A:
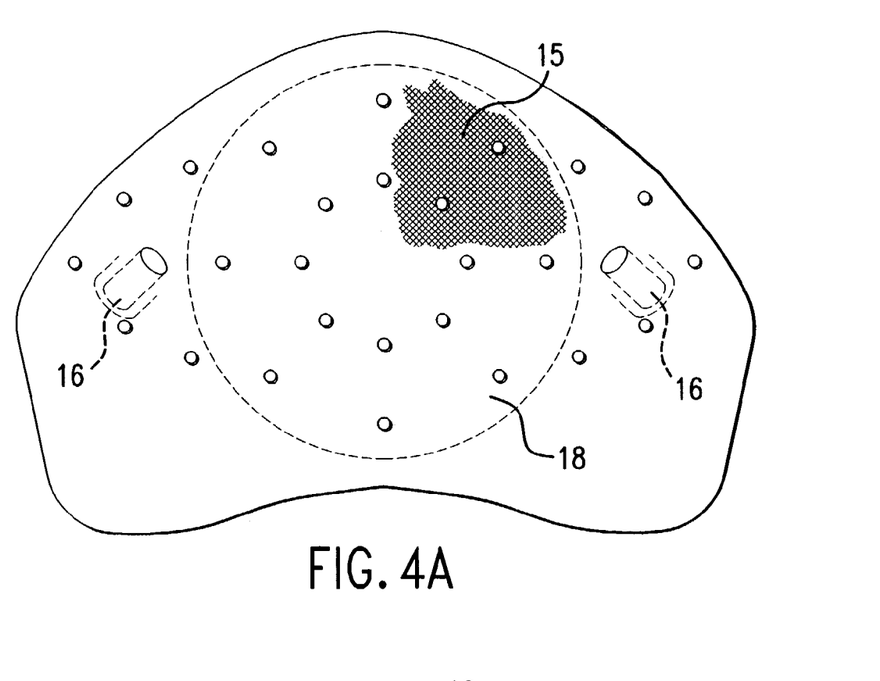
FIG. 4A is a top view of a preferred embodiment of the upper crown plate 11 and the lower crown plate 80 in which the crown plates 80, 11 have a substantial kidney-shape that conforms to the cross-sectional shape of the adjoining vertebral end-plates.
Figure 4B:
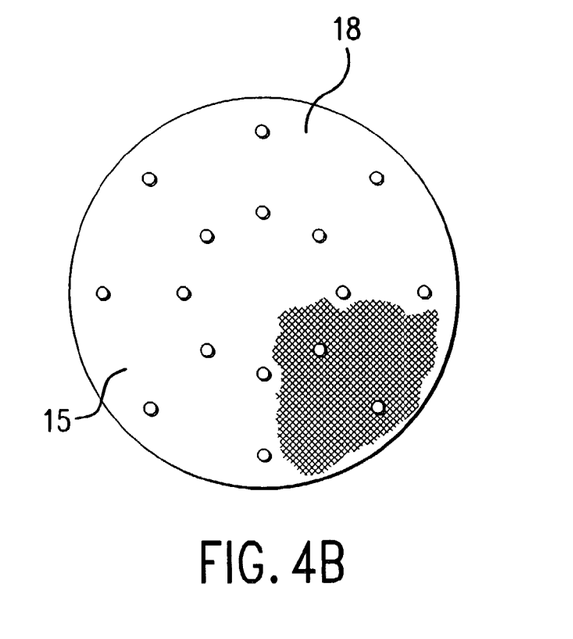
FIG. 4B is an embodiment of the upper crown plate 11 and the lower crown plate 80, in which the crown plates 11, 80 have a more circular shape that conforms to the cross-sectional shape of the excised nucleus pulposus.

The upper crown plate 11 incorporates a sintered titanium or other like metallic planar surface 15 as seen in FIGS. 4A and 4B, with vertebral engaging members or spikes 17 projecting therefrom as seen in FIGS. 1 and 2. Opposite upper surface 18 is lower surface 19 defining a second surface which has an annular groove 22 formed therein, as illustrated in FIG. 1.

The lower crown plate 80 incorporates a mechanism for filling and bleeding fluids into or out of the assembly. In one preferred embodiment, seen in FIGS. 1 and 2, a threaded fill port 84 is contained in the lower crown plate 80 and a fluid channel 85 is formed therethrough. The threaded fill port 84 can be incorporated within the lower crown plate 80, as shown in the embodiment of FIGS. 1 and 2.

Figure 5:
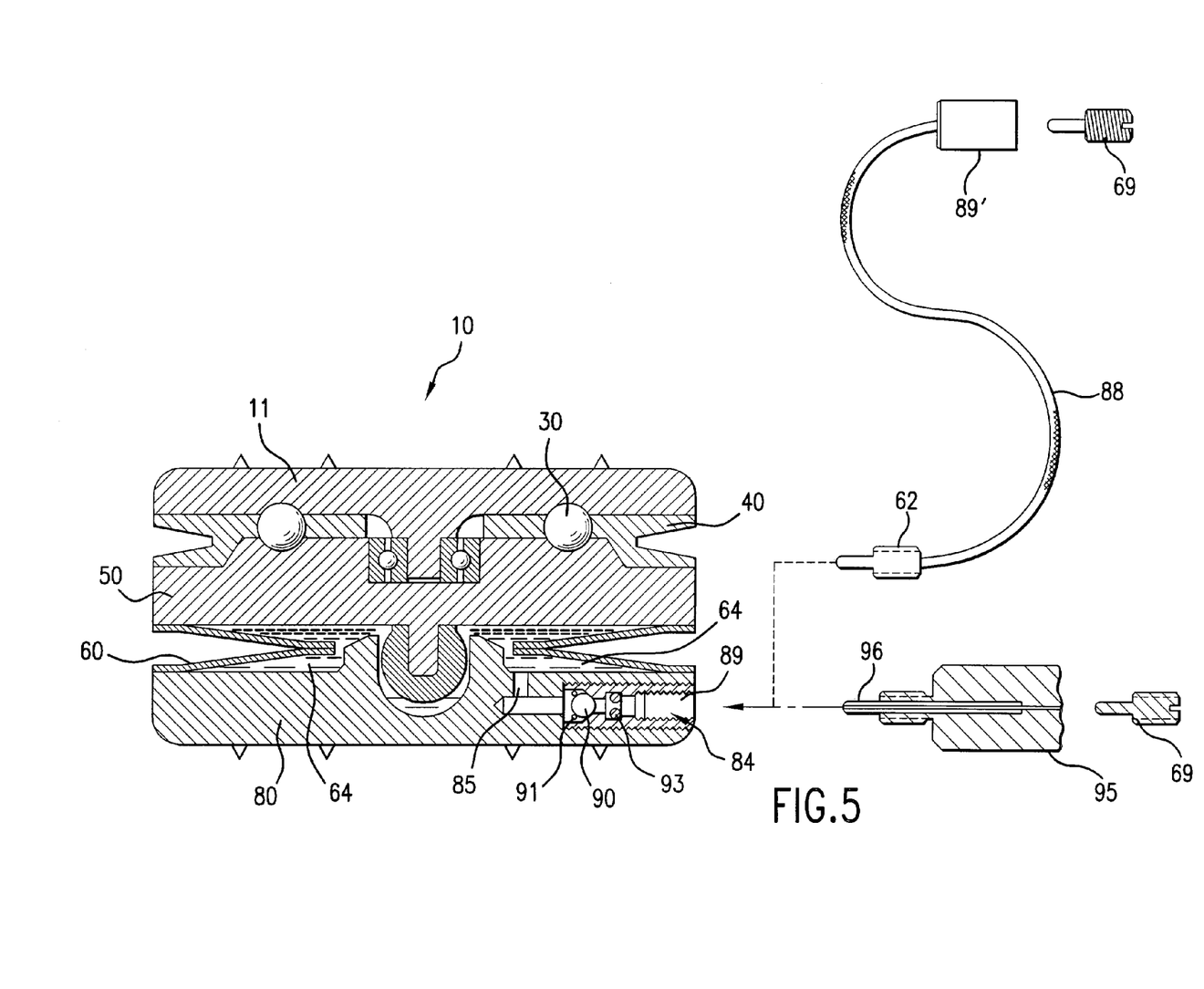
FIG. 5 shows one of the preferred embodiments that includes the valve mechanism 84 with the optional remote valve access components.

Alternatively the fill port 84 may be accessed remotely from the lower crown plate 80, as shown in FIG. 5. As shown, a capillary tube 88 fluidly connects the valve 89 with the lower crown plate member 80. The capillary tube 88 may be formed from either ductile titanium metal, flexible braid reinforced silicone rubber tube, or like material, as shown in FIG. 5. Alternatively, a threaded fill port 84 or a valve and fluid channel may be located in the center bearings plate 50.

As shown in the embodiment illustrated in FIG. 4A, the crown plate members incorporate a layer of sintered titanium 15 on the vertebral engaging surfaces 18 and may be substantially kidney-shaped. The vertebral engaging surfaces 18 have a plurality of spikes 17 projecting therefrom for engaging the vertebral endplates. The spikes 17 laterally affix or set the vertebra engaging members 17 to their respective vertebrae.

The spikes 17 are shown in FIGS. 1 and 2 as having a substantially triangular cross-section. However, the spikes 17 may be of any suitable size or shape for engaging the vertebral endplates, as shown in FIG. 1. The spikes 17 may be formed from sintered titanium, solid titanium, or any other suitable material providing biocompatiblity and both compressive and shear strength. Due to the fact that the spinal cord is especially sensitive to injury and damage, it is necessary that the spikes 17, as well as the other elements forming a spinal prosthetic device 10, such as the center bearings plate and the bellows 60, be formed from strong, resilient and biocompatible materials such as titanium and other like metals or plastics compositions. Sintered titanium, for example, allows for longevity, strength, and no potential for rejection of the elements forming the spinal prosthetic device 10 by the body. Further, the prosthetic element formed from sintered titanium promotes bone growth in and around that projecting element.

Further shown in FIGS. 4A and 4B is the irregular surface 18. The porous surface 18 forms a mesh or sintered surface 15 for permitting the upper crown plate 11 and the lower crown plate 80 to be joined to the vertebrae. In one embodiment illustrated in FIG. 4A, showing a kidney-shaped crown plate vertebral surface, the outer surfaces 18 of crown plates 11, 80 are shaped and sized to substantially match the adjacent vertebral end plate cross-sections, thus reducing the occurrence of heterotopic ossification, also known as lipping, by new bone growth into the intervertebral space that could interfere with the full range of motion of the affected spinal motion segment.

Self-tapping screws (not shown) are passed through the vertebral fixation openings 16 in the crown plates, also illustrated in FIG. 4A, into the contiguous vertebral endplates, the crown plates being further held to the vertebrae 14 by subsequent growth of the bone into the porous surfaces 15. The self-tapping screws can be used to secure the larger kidney-shaped upper crown plate 11 and lower crown plate 80 to their conjoining vertebrae 14. The surgeon, with the use of a separate drill insert bushing, can use bores to first pre-drill a screw diameter hole into the vertebrae prior to installing the self-tapping screw. This configuration can be used when the annulus fibrosus has been removed. The screws provide further stability and strength for implantation of the spinal prosthetic device. The screws may be used in conjunction with spikes 17, as shown in FIG. 4A. A porous surface 18 is also formed on the more circular crown plate members of the embodiment without the vertebral fixation openings and screws, shown in FIG. 4B.

The flexible bellows 60 can be formed from a plurality of washers, formed of titanium or like composition, securely joined together through laser welding, electron beam welding, resistance welding, or some other suitable technique. Similarly, the flexible bellows 60 are joined to the outer surfaces of the center bearings plate 50 and the lower crown plate 80 through laser welding, electron beam welding, or any other suitable method.

The plurality of titanium washers forming the flexible bellows 60 allow for vertical flexibility and axial lengthening and shortening of the bellows, and also act to prevent lateral shearing displacement of the bellows. The sensitivity of the spinal cord to damage requires that the spinal prosthetic device 10 be both flexible along the main vertical axis and very resistant to lateral shear movement, that is, movement that would bend the bellows into a parallelogram shape. A rocking motion of the prosthetic device 10 is desired for more natural movement.

The bellows members 60 permit forward, backward and lateral motion within the spine, and afford axial height flexing about the longitudinal axis by means of the liquid contained therein. The bellows 60 absorbs the imposed stresses by flexing, bending and distention of its convolutions. There is very little rubbing of one component against another, thus eliminating wear on these mechanical parts, and giving the device 10 an extended working life.

Furthermore, the bellows 60 offers both spring-like action while also lending itself as a container to house a fill fluid 64. In bellows systems utilizing Belleville type conical washers made of titanium, hundreds of millions of cycles are routinely imposed without failure. The bellows design incorporates the torsional stability of a coil spring with the tension and compression stability of a leaf spring. Regardless of how the loads are applied, deflection is effected without any of the flexing parts destructively rubbing against one another.

The joined washers forming the bellows 60 provide for not only flexibility along the main axis of the spinal prosthetic device 10, but prevent shear movement in the radial direction. The spinal cord is especially susceptible to injury and damage, and the bellows assembly 60 containing the hydraulic fill fluid 64 prevents the device 10 from being crushed or shifted in the radial direction, thus preventing injury to the aorta or nerves of the spinal cord.

As shown in FIGS. 1 and 2, reversibly displaceable bellows 60 are sealed on one end to center bearings plate 50, and on the other end to the second surface 19 of the lower crown plate 80. Center bearings plate 50 may be made of titanium or any other suitable, strong and rigid metal material, which is weld compatible with bellows 60. Center bearings plate 50 is bonded to the reversibly extendable bellows 60 through welding or any other suitable means. As shown, center bearings plate 50 has a bearing recess 54 and an annular groove 22 formed therein. Furthermore, center bearings plate 50 has formed on its inferior aspect a centrally located dashpot mechanism 70.

In order to allow torsional motion between the conjoined vertebrae, simulating natural spinal movement, the upper crown plate 11 and the center bearings plate 50 rotate around the central axis, rolling on ball bearings 30. There is little friction, heat, or wear produced in the rolling contact between the upper crown plate 11, the center bearings plate 50, and the ball bearings 30 as long as the yield stress of neither the ball bearings 30 nor the annular grooves 22 is exceeded. A silicone grease or other biocompatible lubricant may be present on either surface of the bearing retainer seal 40 in order to add lubrication to the center bearing plate 50 and the upper crown plate 11 with respect to the bearing retainer seal 40.

Bearing retainer seal 40, as shown in FIGS. 1 and 2, incorporates multiple hardened steel ball bearings 30 captured within a biocompatible washer seal material. As shown in FIGS. 1 and 2, a radial thrust bearing assembly 20 is received within the bearing recess 54 of the center bearings plate 50. The ball bearing projections of the bearing retainer seal 40 are received within the annular grooves 22 formed both on the inner second surface of the upper crown plate 19, as well as in the superior surface of the center bearings plate 50.

Ball bearing members 30 of the bearing retainer seal 40 are received within the annular grooves 22 of both the upper crown plate 11 and the center bearings plate 50. The upper crown plate 11 and lower crown plate 80 are assembled together with the bearing retainer seal 40, the center bearings plate 50 and the bellows 60 as seen in FIGS. 1 and 2. The radial thrust bearing assembly forms the rotational coupling between the upper crown plate 11 and the center bearings plate 50, the reversibly displaceable bellows 60, the lower crown plate 80, as well as the center bearings plate 50 are, together, free to rotate with respect to the vertebral upper crown plate 11.

As shown in FIGS. 1 and 2, spikes 17 engage the bone of the vertebrae 14, holding the spinal prosthetic device 10 in place with respect to the spine. The rotation of the lower crown plate 80, the bellows 60 and the center bearings plate 50 with respect to the upper crown plate 11, allows for a fully rotating and articulating motion of the prosthetic device 10 with respect to the adjoining vertebrae 14. Thus, the spinal prosthetic device 10 provides for natural torsional movement of the spine and decreased risk of injury and dislocation of the crown plate members with respect to the vertebrae.

The bellows 60 are comprised of a plurality of conical washers formed of titanium or similar composition. This configuration is set to approximate the final desired distance between the vertebrae 14 and relies on the surgeon to distract the vertebrae 14 with a distractor tool prior to implantation of the device. The device 10 can be sized to fit into the space formerly occupied by the nucleus pulposus when the annulus fibrosus is left intact, or sized with a larger kidney shaped surface 18, illustrated in FIG. 4A, to fit between the vertebrae 14 when both the annulus fibrosus and the nucleus pulposus have been removed.

Furthermore, the bellows assembly 60 are comprised of paired conical washers formed of titanium or like composition. This configuration is pre-expanded to approximate the final desired distance between the vertebrae 14 and relies on the surgeon to distract the vertebrae with a distractor tool prior to positioning and implantation of the device. The device 10 can be sized to fit into the space formerly occupied by the nucleus pulposus when the annulus fibrosus is left intact, or sized with a larger, kidney-shaped contour to fit between the vertebrae 14 when the annulus fibrosus has been removed as part of a total discectomy. When the bellows member 60 is made from two Belleville type washers, as shown in FIGS. 1 and 2, the total number of degrees of spinal motion segment bending/tilting excursion allowed is what is considered normal, approximately 10 degrees.

The spinal prosthetic device 10 may be pre-filled with a substantially incompressible biocompatible fluid at the time of manufacture, wherein the bellows 60 may be pre-expanded to be near the desired final height and, in this embodiment, the surgeon would use a separate distracting tool to spread the two adjacent vertebrae apart before inserting the device 10 into final position.

A dashpot mechanism 70 is incorporated between the center bearings plate 50 and the lower crown plate 80 wherein the dashpot 70 and the spinal prosthetic device 10 are coaxial. The substantially spherical dashpot element 72 extends from the inferior surface of the center bearings plate 50 into the dashpot recess 82 formed on the second, inner surface 19 of the lower crown plate 80. The substantially spherical dashpot element 72 when seated in the dashpot recess 82 is surrounded by fluid in the dashpot cavity 74 formed by the space between the spherical dashpot element 72 and the recess 82. This dashpot cavity fluid is in continuity with the fluid 64 contained within the bellows 60.

Figure 3A:
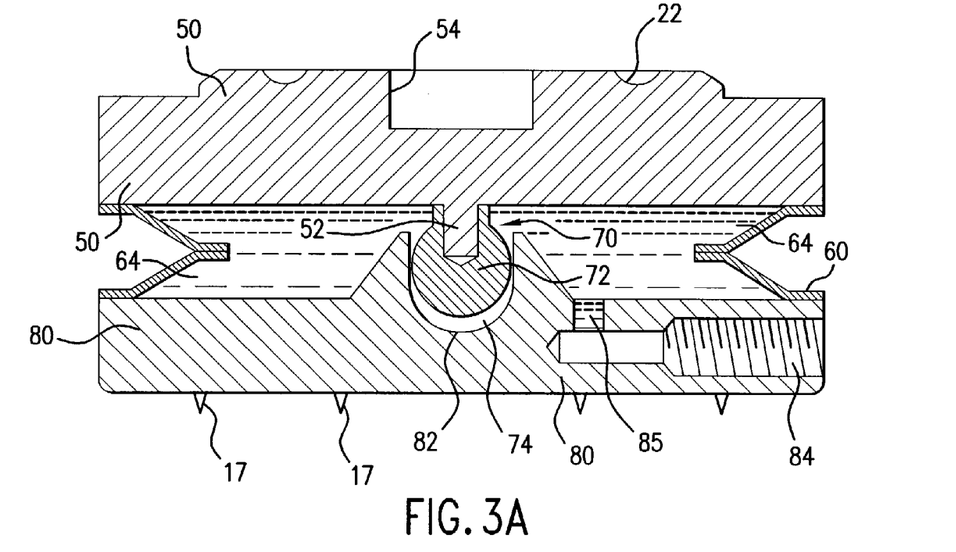
FIG. 3A is a cross-sectional view of a preferred embodiment of the substantially spherical dashpot assembly mechanism 72 of the subject spinal prosthetic device 10.

As seen in FIG. 3A, the substantially spherical dashpot element 72 is fixedly seated on a dashpot mounting post 52, which is formed from the inferior surface of the center bearings plate 50.

Figure 3B:
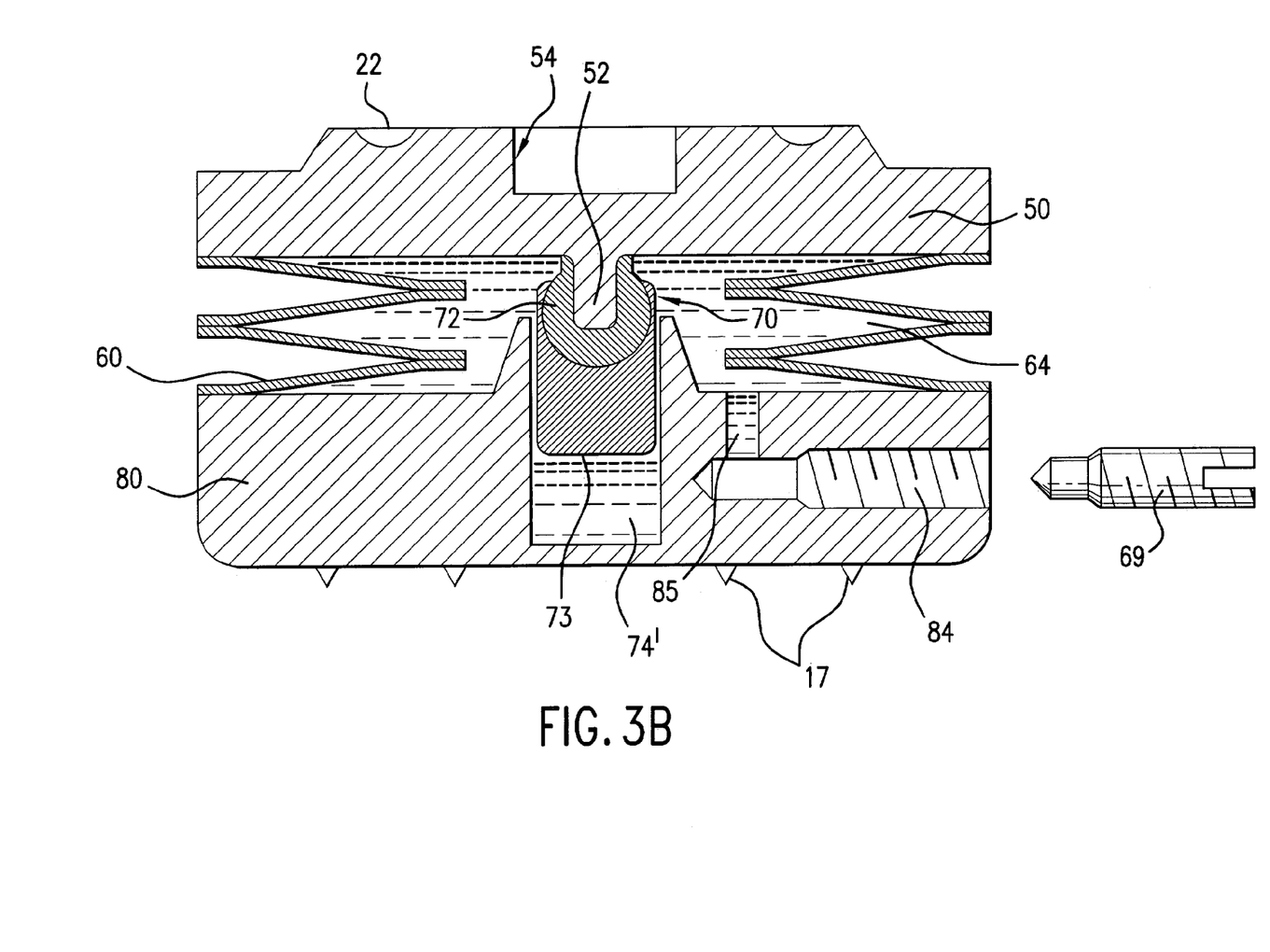
FIG. 3B is a cross-sectional view of an alternative embodiment of the dashpot assembly mechanism 72 of the subject spinal prosthetic device 10 containing two joined bellows 60, in which a cylindrical piston 73 is crimped onto the substantially spherical dashpot element 72, and the dashpot recess 74' is formed to a shape so as to accommodate the cylindrical piston 73 while allowing for fluidic continuity between the dashpot recess 74' and the fluid 64 contained in the bellows chamber.

As may be seen in FIG. 3B, an alternative preferred embodiment includes a cylindrical piston 73 crimped onto the substantially spherical dashpot element 72, with the dashpot recess 74' formed in the inner surface 19 of the lower crown plate with a shape that accommodates the cylindrical piston 73 while allowing fluidic connection between the dashpot recess 74' and the fluid 64 contained in the chamber formed by the bellows 60.

The incorporation of a dashpot mechanism 70 adds further tolerance to sudden and excessive axial force loads, and also constitutes a further means for the device to safely resist shearing forces in the radial direction. By incorporation of a dashpot mechanism 70, the safety and functionality of the spinal prosthetic device 10 is augmented, permitting more vigorous activities which are associated with greater force loads in an axial and radial direction, and further provides an increased margin of safety for shearing forces, thereby further protecting against injury to the spinal cord or nearby vascular structures. The use of the hydraulic dashpot permits dampening of high shock loads, without which the bellows could rupture.

FIGS. 1 and 2 show the preferred embodiment of the prosthetic device 10, wherein the threaded fill port 84 is integral with the lower crown plate 80. Once the threaded fill port 84 is opened by unscrewing and removing a seal screw 69, fill fluid 64 may be injected, pumped or otherwise forced into the device, causing it to expand. When the surgeon wishes to detract the device 10, a relief knob (not shown) is opened and the fill fluid 64 will be removed from the spinal prosthesis device chamber.

An alternative embodiment is shown in FIG. 5, wherein the valve insert 89 is provided with an outer thread and includes a ball check 90 which is biased in the closed position by spring 91. Seal screw 69 is provided as a sealing means after all filling adjustments have been completed. Valve insert 89 has a threaded recess formed therein for receiving the threads of seal screw 69. Also within the recess of valve insert 89 is an O-ring seal 93 for sealingly receiving the seal screw 69, and sealing around the hypodermic needle 96.

Valve insert 89 is provided for the filling of the reversibly extendable bellows 60 with an incompressible liquid, the fill fluid 64. Fluid flows through fluid channel 85 to fill the bellows assembly 60 to a predetermined height, depending upon the desired intervertebral spacing.

FIG. 5 shows the spinal prosthetic device 10 having an alternate filling attachment means. Installed in the threaded port 84, valve insert 89 is integral with the lower crown plate 80 as shown. Hypodermic needle charge fitting 95 is received within valve insert 89. The charge fitting includes the hypodermic needle 96 which passes through O-ring seal 93, effecting a seal. As the fitting 95 is further inserted into valve connector 89, needle 96 pushes the ball check 90 away from its seat and further compresses the spring behind it. Once the ball check 90 is unseated, fill fluid may be injected or pumped into the device 10 thereby causing it to expand. When the surgeon wishes to detract the device 10, the relief knob on the pump (not shown) is opened, and the fill fluid will bleed back into the pump.

FIG. 5 further illustrates extension tubing 88. Extension connector 62 is received within valve insert 89, allowing remote valve insert 89' to be used remote to the valve insert 89. Thus, the prosthetic device 10 may be filled with a substantially incompressible biocompatible fluid either through the threaded fill port 84 formed within the lower crown plate 80 or through the remote extension tubing 88. Extension tubing 88 is preferable for filling and bleeding of fluids from the reversibly extendable bellows 60 when the spinal prosthetic device 10 has already been implanted within the spine of the patient.

When the final intervertebral distance setting has been achieved, the surgeon unscrews the extension connector 62 and, as needle 96 is withdrawn, the ball check 90 closes, effecting a seal before the needle 96 passes out beyond the O-ring 93. In order to make the final seal, the surgeon screws seal screw 69 into the valve insert 89, or the remote valve insert 89' if the extension tubing 88 is employed.

If the surgeon needs to adjust the height of the device 10, he or she may fill or drain fluid from the device 10, that is, either evacuate fluid out or pump extra fluid in, by connecting a hand pump or similarly effective means to the device.

In cases where the surgeon desires to keep the annulus fibrosus intact, but cannot distract the vertebrae to their final position at the time of the surgery, the surgeon can attach a short length of tubing 88, as shown in FIG. 5 to the device 10 and tuck the entire tubing extension 88 inside the incision prior to closing the patient up.

After a clinically appropriate time, the patient may have an incision made on an adjacent area of the flank or back to temporarily externalize the remote filling element 89'. The tubing 88 can be removed after expanding the bellows 60 of device 10 to the final intervertebral distance desired. This could be performed with the aid of real time fluoroscopy. When the final intervertebral span distance has been achieved, the surgeon seals the valve 89, thereby hermetically sealing the fluid 64 contained within the prosthetic device 10.

The spinal prosthetic device 10 may be sized so as to make it adaptable to fit in other regions of the spine, such as the cervical and thoracic regions. Just as the cross-sections of the vertebrae increase in area from the cervical region down to the sacrum, the normal loading encountered increases proportionally. Thus, it follows that the larger is the cross-sectional area of the bellows 60, the lower the imposed stresses will be on the bellows convolutions. The bearing load imposed between the crown plates' vertebral engaging surfaces 18 and the vertebrae 14 will also be lower.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

What is being claimed is:

1. A rotatable and reversibly expandable spinal hydraulic prosthetic device comprising:
   (a) an upper crown plate member for engaging a vertebra;
   (b) at least one center bearings plate member rotationally coupled to said upper crown plate member;
   (c) a lower crown plate member for engaging a vertebra, coupled to said center bearing plate member;
   (d) at least one reversibly displaceable bellows member having a fluid contained therein and sandwiched between said lower crown plate member and said center bearings plate member for resisting shearing force loads between said upper crown plate member and said lower crown plate member; and,
   (e) a dashpot mechanism interposed between said center bearings plate and said lower crown plate member for dampening shock loads.

2. The rotatable and reversibly expandable spinal hydraulic prosthetic device as recited in claim 1 wherein said upper crown plate includes a first vertebra engaging surface for joining said upper crown plate to a vertebra, and includes a second bearing surface opposing said first vertebra engaging surface.

3. The rotatable and reversibly expandable spinal hydraulic prosthetic device as recited in claim 2 wherein said second bearing surface of said upper crown plate member has an annular groove formed therein.

4. The rotatable and reversibly expandable spinal hydraulic prosthetic device as recited in claim 3 wherein said center bearings plate member has a first upper surface with an annular groove formed therein.

5. The rotatable and reversibly expandable spinal hydraulic prosthetic device as recited in claim 4 further comprising a bearings retainer seal member disposed between said upper crown plate member and said center bearings plate member, said bearings retainer seal member having a plurality of ball bearings annularly positioned thereon and received within said annular groove of said second bearing surface of said upper crown plate member and said annular groove of said center bearings plate member.

6. The rotatable and reversibly expandable spinal hydraulic prosthetic device as recited in claim 2 wherein said lower crown plate member has a first vertebra engaging surface for joining said lower crown plate to a vertebra, and includes a second opposing surface being connected to an end of said reversibly displaceable bellows member, said lower crown plate member having a fluid channel formed therethrough for permitting said displaceable bellows member to be filled with fluid and for evacuation of said fluid.

7. The rotatable and reversibly expandable spinal hydraulic prosthetic device as recited in claim 6 wherein said lower crown plate member includes a valve member in fluid communication with said fluid channel for selectively sealing said fluid channel.

8. The rotatable and reversibly expandable spinal hydraulic prosthetic device as recited in claim 6 wherein an extension tubing is coupled with said lower crown plate member for fluid adjustment of said reversibly displaceable bellows member.

9. The rotatable and reversibly expandable spinal hydraulic prosthetic device as recited in claim 6 wherein each of said first vertebra engaging surfaces of said upper crown plate member and said lower crown plate member has at least one fixation opening formed therethrough for receiving securing members, joining each to the other.

10. The rotatable and reversibly expandable spinal hydraulic prosthetic device as recited in claim 6 wherein said first vertebra engaging surfaces of the upper crown plate member and the lower crown plate member each includes a plurality of engaging members or spikes projecting therefrom for securing said first vertebra engaging surfaces of said upper crown plate member and said lower crown plate member to respective endplates of a patient's successive vertebrae.

11. The rotatable and reversibly expandable spinal hydraulic prosthetic device as recited in claim 6 wherein said fluid channel is in fluid communication with a valve assembly.

12. The rotatable and reversibly expandable spinal hydraulic prosthetic device as recited in claim 11 wherein said valve assembly is positioned remotely from said lower crown plate member.

13. The rotatable and reversibly expandable spinal hydraulic prosthetic device as recited in claim 1 wherein said dashpot mechanism includes a dashpot element fixedly located on a surface of said center bearing plate member and seated in a non-contiguous manner within a dashpot recess that is formed in a corresponding surface of the lower crown plate member.

14. The rotatable and reversibly expandable spinal hydraulic prosthetic device as recited in claim 13 wherein a dashpot cavity is formed between said dashpot element and said dashpot recess, wherein said dashpot cavity is in fluid communication with the fluid within said bellows member.

15. The rotatable and reversibly expandable spinal hydraulic prosthetic device as recited in claim 1 including at least one bearing retainer seal member, said bearing retainer seal member having a radial thrust bearing assembly, said bearing retainer seal member being rotationally coupled to said upper crown plate member and said center bearings plate member.

16. The rotatable and reversibly expandable spinal hydraulic prosthetic device as recited in claim 15 wherein said bellows member firmly attaches to said center bearings plate on a first end thereof, said center bearings plate having a bearing recess formed on a second end therein, said bearing recess receiving said radial bearing assembly of said bearing retainer seal member, and said bearing retainer seal member being contiguous and rotatable with respect to said center bearings plate member.

17. The rotatable and reversibly expandable spinal hydraulic prosthetic device as recited in claim 1 wherein said fluid is an incompressible fluid.

18. The rotatable and reversibly expandable spinal hydraulic prosthetic device as recited in claim 1 wherein said bellows member is formed as one integral unit.

19. The rotatable and reversibly expandable spinal hydraulic prosthetic device as recited in claim 1 wherein said bellows member is formed from a plurality of washers joined each to the other.

20. The rotatable and reversibly expandable spinal hydraulic prosthetic device as recited in claim 1 wherein a patient's adjacent vertebrae are adjustably distracted by selective in situ hydraulic filling of said reversibly displaceable bellows member.

21. A rotatable, flexible spinal hydraulic prosthetic device, comprising:
 (a) an upper crown plate member for engaging a patient's vertebra;
 (b) a lower crown plate member coupled to said upper crown plate for engaging a patient's vertebra;
 (c) at least one center bearings plate member disposed between said upper crown plate member and said lower crown plate member, said center bearings plate member being rotationally coupled to said upper crown plate member;
 (d) at least one set of biocompatible metallic bellows being positionally located between and coupled to said center bearings plate member and said lower crown plate member, said bellows containing a substantially incompressible biocompatible fluid, wherein said bellows is axially displaceable in response to axial force loads, and flexes laterally as well as in ventral or dorsal directions in response to bending loads;
 (e) a dashpot mechanism interposed between said center bearings plate and said lower crown plate member; and,
 (f) at least one set of thrust and radial bearings disposed between said upper crown plate member and said center bearings plate member for permitting rotation of said upper crown plate member relative to said lower crown plate member in response to torque loads.

22. The rotatable, flexible spinal hydraulic prosthetic device as recited in claim 21 wherein said upper crown-plate includes a first vertebra engaging surface for joining said upper crown plate to a patient's vertebra, and includes a second bearing surface opposing said first vertebra engaging surface.

23. The rotatable, flexible spinal hydraulic prosthetic device as recited in claim 22 wherein said lower crown plate member has a first vertebra engaging surface for joining said lower crown plate to a patient's vertebra, and includes a second opposing surface being connected to an end of said bellows, said lower crown plate member having a fluid channel formed therethrough for permitting said bellows to be filled with said biocompatible fluid and for evacuation of said biocompatible fluid.

24. The rotatable, flexible spinal hydraulic prosthetic device as recited in claim 23 wherein said first vertebra engaging surfaces of the upper crown plate member and the lower crown plate member each includes a plurality of engaging members or spikes projecting therefrom for securing said first vertebra engaging surfaces of said upper crown plate member and said lower crown plate member to respective endplates of a patient's successive vertebrae.

25. The rotatable, flexible spinal hydraulic prosthetic device as recited in claim 23 wherein each of said first vertebra engaging surfaces of said upper crown plate member and said lower crown plate member has at least one fixation opening formed therethrough for receiving securing members, joining each to the other.

26. The rotatable, flexible spinal hydraulic prosthetic device as recited in claim 23 wherein said dashpot mechanism includes a dashpot element fixedly located on a surface of said center bearing plate member and seated in a non-contiguous manner within a dashpot recess that is formed in said second surface of the lower crown plate member.

27. The rotatable, flexible spinal hydraulic prosthetic device as recited in claim 26 wherein a dashpot cavity is formed between said dashpot element and said dashpot recess, wherein said dashpot cavity is in fluid communication with said biocompatible fluid within said bellows.

28. The rotatable, flexible spinal hydraulic prosthetic device as recited in claim 22 further comprising at least one bearing retainer seal member, said bearing retainer seal member having a radial thrust bearing assembly, said bearing retainer seal member being rotationally coupled to said upper crown plate member and said center bearings plate member.

29. The rotatable, flexible spinal hydraulic prosthetic device as recited in claim 28, wherein said bellows firmly attaches to a said center bearings plate on a first end thereof, said center bearings plate having a bearing recess formed on a second end therein, said bearing recess receiving said radial thrust bearing assembly of said bearing retainer seal member, and said bearing retainer seal member being contiguous and rotatable with respect to said center bearings plate member.

30. The rotatable, flexible spinal hydraulic prosthetic device as recited in claim 28 wherein said second bearing surface of said upper crown plate member has an annular groove formed therein.

31. The rotatable, flexible spinal hydraulic prosthetic device as recited in claim 30 wherein said bearings retainer seal member has a plurality of ball bearings annularly positioned thereon and received within said annular groove of said second bearing surface of said upper crown plate member and said annular groove of said center bearings plate member.

* * * * *